(12) United States Patent
Nishikata et al.

(10) Patent No.: US 9,170,220 B2
(45) Date of Patent: Oct. 27, 2015

(54) X-RAY ANALYZER

(71) Applicant: HORIBA, Ltd., Kyoto (JP)

(72) Inventors: Kentaro Nishikata, Kyoto (JP); Satoshi Ohashi, Kyoto (JP); Takashi Komatsubara, Kyoto (JP)

(73) Assignee: HORIBA, LTD (JP)

( * ) Notice: Subject to any disclaimer, the term of this patent is extended or adjusted under 35 U.S.C. 154(b) by 0 days.

(21) Appl. No.: 14/359,498

(22) PCT Filed: Dec. 5, 2012

(86) PCT No.: PCT/JP2012/081436
§ 371 (c)(1),
(2) Date: May 20, 2014

(87) PCT Pub. No.: WO2013/084904
PCT Pub. Date: Jun. 13, 2013

(65) Prior Publication Data
US 2014/0326881 A1    Nov. 6, 2014

(30) Foreign Application Priority Data
Dec. 9, 2011 (JP) ................................ 2011-270689

(51) Int. Cl.
*G01N 23/225* (2006.01)
*G01N 23/223* (2006.01)

(52) U.S. Cl.
CPC .......... *G01N 23/2252* (2013.01); *G01N 23/223* (2013.01); *G01N 2223/076* (2013.01)

(58) Field of Classification Search
USPC .................................. 250/305, 306, 307, 310
See application file for complete search history.

(56) References Cited

U.S. PATENT DOCUMENTS

| 4,519,092 A | 5/1985 | Albert |
| 5,044,001 A | 8/1991 | Wang |

(Continued)

FOREIGN PATENT DOCUMENTS

| EP | 1672672 A2 | 6/2006 |
| JP | 2003-187735 A | 7/2003 |

(Continued)

OTHER PUBLICATIONS

International Search Report for International Application PCT/JP2012/081436; Date of Mailing Feb. 26, 2013, with English translation.

(Continued)

*Primary Examiner* — Kiet T Nguyen
(74) *Attorney, Agent, or Firm* — Cantor Colburn LLP

(57) ABSTRACT

The X-ray analyzer repeats scanning of a sample by an electron beam from an electron gun (beam source), detects a characteristic X-ray from the sample by an X-ray detector, generates an element distribution image of the sample by a signal processor every scanning, and stores a plurality of element distribution images in a sequential order. Temporal changes of the element distribution image of the sample are obtained. Moreover, by moving a stage by a moving unit concurrently with the scanning, an element distribution image of the sample where the scanning position is varied is obtained. By generating the element distribution image while varying the scanning position, positioning of the range where the element distribution image is to be obtained on the sample can be quickly performed based on the element distribution image itself.

7 Claims, 4 Drawing Sheets

(56) References Cited

U.S. PATENT DOCUMENTS

| | | | |
|---|---|---|---|
| 6,051,834 A * | 4/2000 | Kakibayashi et al. | 250/311 |
| 2005/0072919 A1 | 4/2005 | Meyer et al. | |
| 2006/0188060 A1 | 8/2006 | Bertozzi et al. | |
| 2006/0219907 A1 * | 10/2006 | Ogashiwa et al. | 250/310 |

FOREIGN PATENT DOCUMENTS

| | | |
|---|---|---|
| JP | 2004-191183 A | 7/2004 |
| JP | 2004191183 A | 7/2004 |
| JP | 2006-47206 A | 2/2006 |
| JP | 4136635 B2 | 8/2008 |
| JP | 2010-164442 A | 7/2010 |

OTHER PUBLICATIONS

Extended European Search Report issued in the European patent Application No. 12855929.1; Mailed: Jun. 17, 2015.

* cited by examiner

X-RAY ANALYZER

CROSS REFERENCE TO RELATED APPLICATIONS

This is the U.S. national stage of application No. PCT/JP2012/081436 filed on Dec. 5, 2012. Priority under 35 U.S.C. §119(a) and 35 U.S.C. §365(b) is claimed from Japanese Application No. 2011-270689, filed on Dec. 9, 2011, the disclosure of which is also incorporated herein by reference.

BACKGROUND

1. Technical Field

The present invention relates to an X-ray analyzer that scans a sample by a beam, detects an X-ray generated on the sample and analyzes the distribution of the components of the sample.

2. Description of Related Art

The X-ray analysis is an analysis method in which a beam such as an electron beam or an X-ray is applied to a sample, a characteristic X-ray or an X-ray fluorescence generated on the sample is detected and a qualitative analysis or a quantitative analysis of the elements contained in the sample is performed based on the spectrum of the characteristic X-ray or the X-ray fluorescence. Moreover, an element distribution image representative of a distribution of the elements contained in the sample can be obtained by detecting the characteristic X-ray or the X-ray fluorescence while scanning the sample by the beam. An X-ray analyzer using an electron beam is sometimes incorporated in an electron microscope. Japanese Patent No. 4,136,635 discloses an example of the art of generating an element distribution image by an X-ray analysis.

SUMMARY OF THE INVENTION

In the conventional X-ray analyzers, the element distribution image is generated as a still image. When a range where the element distribution image is to be obtained is positioned on the sample, the positioning is performed based on an image other than the element distribution image such as an electron microscopic image or an optical microscopic image of the sample. However, after the image other than the element distribution image is generated, it is necessary to generate the element distribution image, check the generated element distribution image and repeat the work until a desired element distribution image is generated, which requires labor and time. Moreover, since the contents of the obtained information is different between the image other than the element distribution image and the element distribution image, the range where the element distribution image is to be obtained cannot be always determined from the image other than the element distribution image. Consequently, with the conventional X-ray analyzers, it is difficult to perform the positioning quickly. In addition, with the conventional X-ray analyzers, since the element distribution image is generated as a still image, it is impossible to perform the observation of temporal changes such as the observation of a moving sample or the observation of an element moving in a sample.

The present invention is made in view of such circumstances, and an object thereof is to provide an X-ray analyzer that enables quick positioning and enables the observation of temporal changes by repeating the generation of an element distribution image.

An X-ray analyzer according to the present invention is characterized by comprising: a beam source; a sample holder; a scanning unit for scanning repetitively a sample held by the sample holder, by a beam from the beam source; an X-ray detector that is disposed in a position between the beam source and the sample holder, and detects an X-ray generated on the sample scanned by the scanning unit; a generation unit for generating an element distribution image representative of a distribution of an element contained in the sample, based on a result of the detection by the X-ray detector, every time the scanning unit scans the sample; and a storage unit for storing a plurality of element distribution images generated by the generation unit, in associated with information representative of a sequential order of generation of the element distribution images.

In the present invention, the X-ray analyzer repetitively scans the sample by the beam, generates the element distribution image representative of the distribution of the elements contained in the sample every scanning, and stores a plurality of element distribution images in associated with information representative of the sequential order of the generation. Temporal changes of the element distribution image of the sample are recorded.

The X-ray analyzer according to the present invention, is characterized by further comprising: a display unit; and a clock unit for measuring a time elapsed from a specific time point, wherein the storage unit stores information representative of the measured elapsed time as the information representative of the sequential order, and the display unit sequentially displays the element distribution images stored in the storage unit according to the measured elapsed time.

In the present invention, the X-ray analyzer sequentially displays a plurality of element distribution images in the order corresponding to the elapsed time. Changes of the element distribution image according to the passage of time are displayed.

The X-ray analyzer according to the present invention, is characterized in that wherein the display unit the element distribution image generated by the generation unit and updating the displayed element distribution image every time the generation unit generates the element distribution image.

In the present invention, the X-ray analyzer displays the element distribution image, and updates the displayed element distribution image every time the scanning of the sample by the beam and the generation of the element distribution image are performed. The element distribution image of the sample is displayed in real time.

The X-ray analyzer according to the present invention, is characterized by further comprising a moving unit for moving the sample holder concurrently with the operations of the scanning unit and the generation unit.

The X-ray analyzer according to the present invention, is characterized by further comprising a moving unit for moving the sample holder concurrently with the operations of the scanning unit and the generation unit.

The X-ray analyzer according to the present invention, is characterized by further comprising: an accept unit for accepting an instruction for moving the sample; a moving unit for moving the sample holder; and a shifting unit for shifting a range where the scanning unit scans on the sample, by causing the moving unit to move the sample holder according to the instruction accepted by the accept unit.

In the present invention, the X-ray analyzer moves the sample concurrently with the scanning of the sample by the beam and the generation of the element distribution image. Temporal changes of the element distribution image of a moving sample are recorded.

The X-ray analyzer according to the present invention, is characterized by further comprising a change creating unit for creating a physical or a chemical change on the sample held by the sample holder concurrently with the operations of the scanning unit and the generation unit.

The X-ray analyzer according to the present invention, is characterized in that the X-ray detector includes a plurality of X-ray sensors.

In the present invention, the X-ray analyzer causes a physical or a chemical change on the sample concurrently with the scanning of the sample by the beam and the generation of the element distribution image. The physical or the chemical change of the element distribution image of the sample is recorded.

In the present invention, by checking temporal changes of the element distribution image of the sample, positioning of the range where the element distribution image is to be obtained on the sample can be performed based on the element distribution image itself, which enables quick positioning. In addition, the present invention produces excellent effects such that temporal changes of the element distribution image of the sample can be observed.

The above and further objects and features of the invention will more fully be apparent from the following detailed description with accompanying drawings.

DETAILED DESCRIPTION

Hereinafter, the present invention will be concretely described based on the drawings showing embodiments thereof.

(Embodiment 1)

Figure 1:
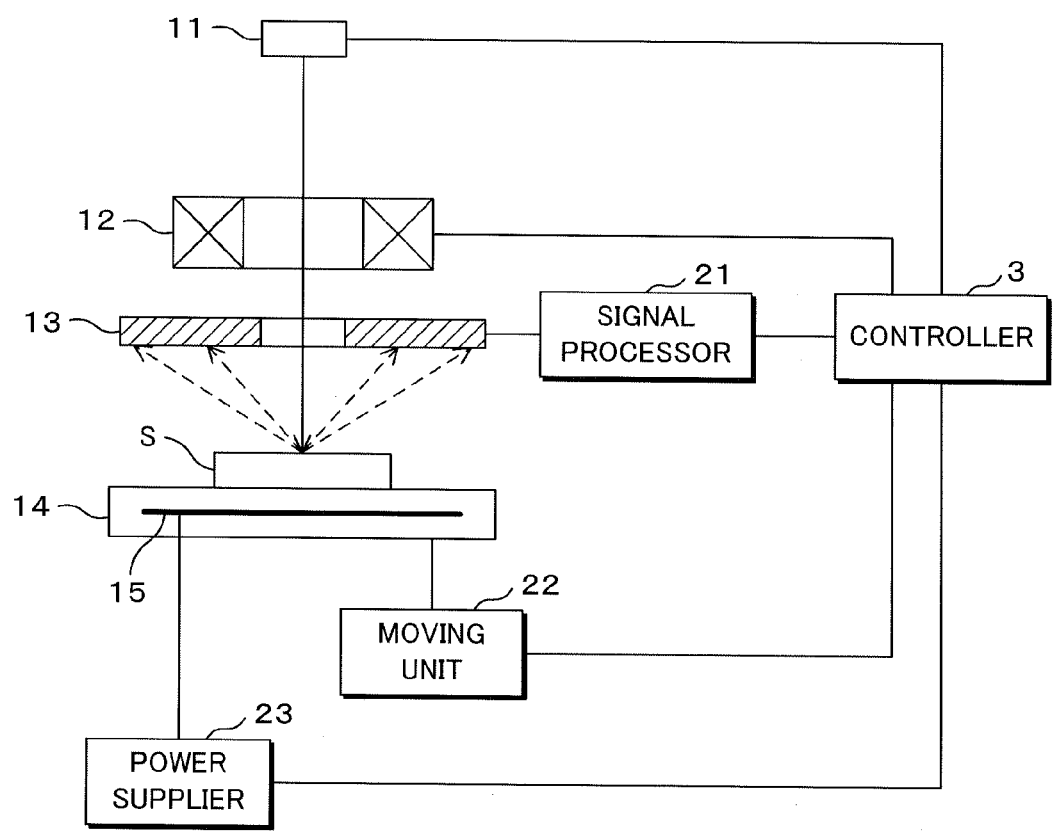
FIG. 1 is a block diagram showing the configuration of an X-ray analyzer according to Embodiment 1.

FIG. 1 is a block diagram showing the configuration of an X-ray analyzer according to Embodiment 1. The X-ray analyzer is provided with an electron gun (beam source) 11 that applies an electron beam (beam) to a sample S, an electron lens system 12, and a stage (sample holder) 14 where the sample S is mounted. The electron lens system 12 includes a scanning coil that changes the direction of the electron beam, and corresponds to the scanning unit of the present invention. The electron gun 11 and the electron lens system 12 are connected to a controller 3 that controls the entire X-ray analyzer. While FIG. 1 illustrates a plane sample S, the X-ray analyzer is also capable of measuring samples of other shapes such as a sphere. While the electron gun 11, the electron lens system 12 and the stage 14 are coaxial in FIG. 1, there are cases where the electron gun 11, the electron lens system 12 and the stage 14 are not coaxial such as when the stage 14 is inclined.

An X-ray detector 13 is disposed between the electron lens system 12 and the stage 14. The X-ray detector 13 is formed in a configuration having a hole for passing an electron beam therethrough. Moreover, the X-ray detector 13 is configured by using an SDD (silicon drift detector) as an X-ray sensor. For example, the X-ray detector 13 has a configuration in which a plurality of SDDs are mounted on a board having a hole and the SDDs are disposed so as to surround the hole. In FIG. 1, a cross section of the X-ray detector 13 is shown. The X-ray detector 13 is disposed in a position where the electron beam passes through the hole, and the X-ray incident surface is disposed orthogonal to the optical axis of the electron beam. Moreover, a non-illustrated cooling device such as a Peltier device is attached to the X-ray detector 13. Under a condition where the sample S is mounted on the stage 14, the X-ray detector 13 is disposed in front of the surface of the sample S irradiated with the electron beam. According to a control signal from the controller 3, the electron gun 11 emits an electron beam, the electron lens system 12 determines the direction of the electron beam, and the electron beam passes through the hole of the X-ray detector 13 to irradiate the sample S on the stage 14. On the sample S, a characteristic X-ray generated at the part irradiated with the electron beam, and the generated characteristic X-ray is detected by the X-ray detector 13. In FIG. 1, the electron beam is represented by a solid arrow, whereas the characteristic X-ray is represented by broken arrows. The X-ray detector 13 outputs a signal proportional to the energy of the detected characteristic X-ray.

A signal processor 21 that processes the outputted signal is connected to the X-ray detector 13. The signal processor 21 accepts the signal outputted by the X-ray detector 13, counts the signal of each value, and performs the processing of obtaining the relationship between the energy of the characteristic X-ray detected by the X-ray detector 13 and the number of counts, that is, the spectrum of the characteristic X-ray. The signal processor 21 is connected to the controller 3.

By the electron lens system 12 successively changing the direction of the electron beam, the electron beam is applied to the sample S while scanning the sample S. By the electron beam scanning the sample S, the electron beam is successively applied to each part in the scanning range of the sample S. As the electron beam scans the sample S, the characteristic X-ray generated at each part on the sample S is successively detected by the X-ray detector 13. The signal processor 21 successively performs signal processing to thereby successively generate the spectrum of the characteristic X-ray generated at each part on the sample S. Moreover, the signal processor 21 calculates the amounts of various elements contained in the sample S from the spectrum of the characteristic X-ray and associates the amounts of elements obtained from the spectrum of the characteristic X-ray generated at each part on the sample S, with each part on the sample S, thereby generating an element distribution image representative of the distribution of the elements on the sample S. The element distribution image is an image where the amounts of elements contained in each part on the sample S are represented by colors or by shades of gray. The signal processor 21 outputs the data of the generated element distribution image to the controller 3.

A moving unit 22 such as a stepping motor that moves the stage 14 is coupled to the stage 14. The moving unit 22 moves the stage 14 in the horizontal direction. The moving unit 22 is connected to the controller 3, and has its operation controlled by the controller 3. Moreover, a heater 15 that heats the sample S mounted on the stage 14 is incorporated in the stage 14. A power supplier 23 for supplying power to cause the heater 15 to generate heat is connected to the heater 15. The power supplier 23 is connected to the controller 3, and has its operation controlled by the controller 3. Of the components of the X-ray analyzer, at least the electron gun 11, the electron lens system 12, the X-ray detector 13 and the stage 14 are placed in a non-illustrated vacuum chamber. The vacuum chamber is made of a material that blocks the electron beam and X-rays, and while the X-ray analyzer is operating, the vacuum chamber is held evacuated.

Figure 2:
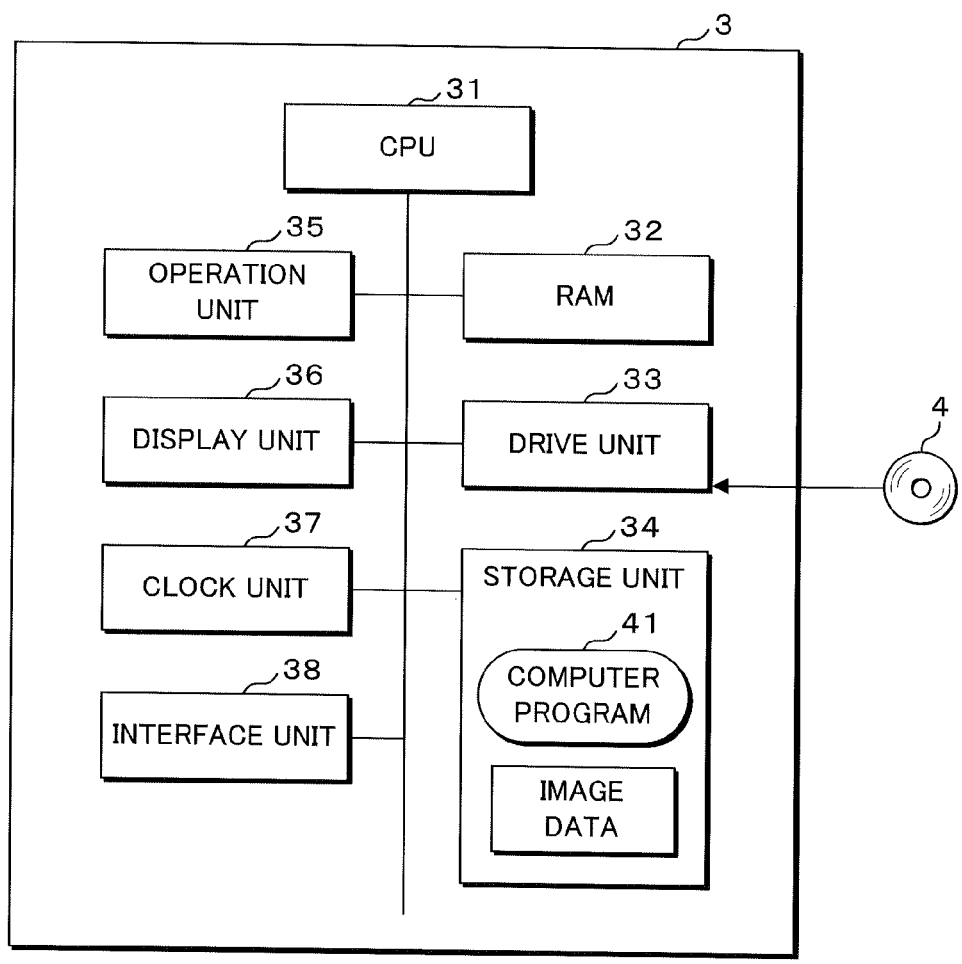
FIG. 2 is a block diagram showing the internal configuration of a controller.

FIG. 2 is a block diagram showing the internal configuration of the controller 3. The controller 3 is configured by using a computer such as a personal computer. The controller 3 is provided with a CPU (central processing unit) 31 that performs a calculation, a RAM (random access memory) 32 that stores temporal data generated in association with the calculation, a drive unit 33 that reads information from a recording medium 4 such as an optical disk, and a non-volatile storage unit 34 such as a hard disk. Moreover, the controller 3 is provided with an operation unit 35 such as a keyboard or a mouse that accepts a user operation, a display unit 36 such as a liquid crystal display, a clock unit 37 that measures time, and an interface unit 38. The electron gun 11, the electron lens system 12, the signal processor 21, the moving unit 22 and the power supplier 23 are connected to the interface unit 38. The CPU 31 causes the drive unit 33 to read a computer program 41 recorded on the recording medium 4, and stores the read computer program 41 into the storage unit 34. The computer program 41 is loaded from the storage unit 34 into the RAM 32 as required, and according to the loaded computer program 41, the CPU 31 executes processing necessary for the X-ray analyzer. The computer program 41 may be downloaded from the outside of the controller 3. Moreover, the storage unit 34 stores image data where the data of the element distribution image inputted from the signal processor 21 and the data representative of the time measured by the clock unit 37 are associated with each other.

Figure 3:
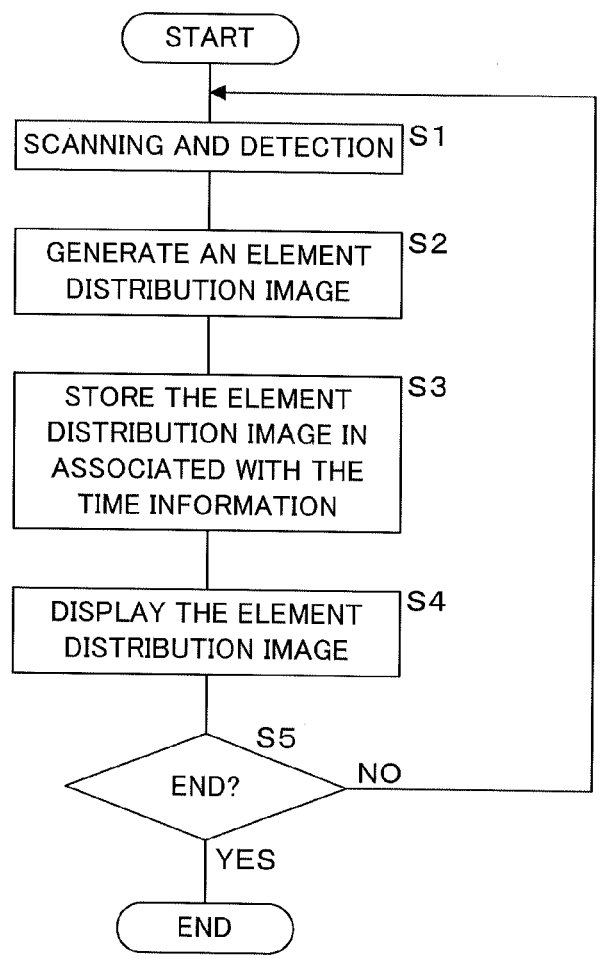
FIG. 3 is a flowchart showing the procedure of the X-ray analysis processing executed by the X-ray analyzer.

FIG. 3 is a flowchart showing the procedure of the X-ray analysis processing executed by the X-ray analyzer. In response to a trigger such as an instruction accepted by the operation unit 35 by a user operation or the time measured by the clock unit 37, the CPU 31 transmits a control signal from the interface unit 38 to the electron gun 11 and the electron lens system 12, whereby the X-ray analyzer starts the processing. At this time, the clock unit 37 starts the measurement of the time elapsed from the generation of the trigger. The electron gun 11 emits an electron beam and the electron lens system 12 adjusts the direction of the electron beam according to the control from the controller 3, whereby the electron beam scans the sample S and the X-ray detector 13 detects the characteristic X-ray (S1). The electron lens system 12 two-dimensionally scans a range of a fixed size on the sample S. Since the X-ray detector 13 is disposed between the electron lens system 12 and the stage 14 and close to the sample S, the characteristic X-ray generated on the sample S is incident on the X-ray detector 13 at area in a large solid angle. In the conventional X-ray analyzers, the X-ray detector is disposed beside the electron lens system, and the solid angle of the characteristic X-ray incident on the X-ray detector is small. The solid angle of the characteristic X-ray incident on the X-ray detector 13 is larger than in the conventional X-ray analyzers, and the characteristic X-ray incident on the X-ray detector 13 makes up a significant larger proportion of the characteristic X-ray generated on the sample S by the electron beam application than in the conventional X-ray analyzers. Consequently, the intensity of the characteristic X-ray detected by the X-ray detector 13 is higher than in the conventional X-ray analyzers.

The X-ray detector 13 outputs a signal corresponding to the energy of the detected characteristic X-ray to the signal processor 21. The signal processor 21 successively generates the spectrum of the characteristic X-ray generated at each part on the sample S in accordance with the progress of the scanning, and generates the element distribution image when the scanning ends with a predetermined unit such as the frame, the line or the pixel (S2). Since the intensity of the characteristic X-ray detected by the X-ray detector 13 is higher than in the conventional X-ray analyzers, the signal outputted by the X-ray detector 13 per unit time is increased, so that the S/N (signal/noise) ratio of the spectrum of the characteristic X-ray is improved. For this reason, even if the rate of generation of the element distribution image is made higher than in the conventional X-ray analyzers, an element distribution image can be generated with a contrast and quality equal to those in the conventional X-ray analyzers. Consequently, the electron beam scanning and the element distribution image generation can be performed at a higher speed than in the conventional X-ray analyzers while the quality of the element distribution image is maintained equal to that in the conventional X-ray analyzers.

The signal processor 21 outputs the data of the generated element distribution image to the controller 3, and the data of the element distribution image is inputted to the interface unit 38 of the controller 3. The CPU 31 stores into the storage unit 34 the image data where the inputted data of the element distribution image and the time information representative of the time measured by the clock unit 37 are associated with each other (S3). The time information includes data representative of the elapsed time from the time point of generation of the processing start trigger. The elapsed time is a time elapsed until a time point associated with the generation of each individual element distribution image such as the time point of end of the scanning or the time point of generation of the element distribution image. Moreover, the time information may include data representative of the time elapsed from the time point of generation of the former element distribution image to the time point of generation of each individual element distribution image. Moreover, the time information may include data representative of the date and the time. By associating the time information and the data of the element distribution image with each other, the sequential order of generation of each of a plurality of element distribution images is recorded. Then, based on the inputted data of the element distribution image, the CPU 31 displays the element distribution image on the display unit 36 (S4). At step S4, when the element distribution image has already been displayed, the displayed element distribution image is updated to a new element distribution image. By the processing at steps S1 to S4, the element distribution image of the sample S is displayed every time the sample S is scanned by the electron beam. Since the scanning by the electron beam is made faster, the element distribution image of the sample S is displayed on the display unit 36 substantially in real time. Then, the CPU 31 determines whether or not it is time to end the X-ray analysis processing such that an end instruction has been accepted by the operation unit 35 by a user operation or that a predetermined time has elapsed (S5). When it is not time to end the processing yet (S5: NO), the CPU 31 returns the processing to step S1. When it is time to end the processing (S5: YES), the CPU 31 ends the X-ray analysis processing.

By the processing at steps S1 to S5, the X-ray analyzer repeats the scanning of the sample S by the electron beam, and every scanning, the element distribution image of the sample S is displayed on the display unit 36 substantially in real time. Concurrently with the processing at steps S1 to S5, the CPU 31 outputs a control signal to the moving unit 22 according to an instruction accepted by the operation unit 35 by a user operation, and the moving unit 22 moves the stage 14 according to the control signal. The sample S moves according to the movement of the stage 14, the position where scanning is performed on the sample S is changed, and the element distribution image of the sample S where the scanning position is changed is displayed on the display unit 36 in real time. This enables the user to change the position where the element distribution image is obtained on the sample S, by operating the operation unit 35 while viewing the displayed element distribution image. Consequently, the range where the element distribution image is to be obtained can be positioned on the sample S based on the element distribution image itself. Since positioning based on the element distribution image itself is possible, quick positioning of the range where the element distribution image is to be obtained on the sample S is possible such as finding out a target element from the element distribution image and obtaining an element distribution image of a range where the element can be sufficiently observed.

Moreover, the X-ray analyzer stores in the storage unit 34 the image data where the data of the element distribution image and the time information are associated with each other. The image data includes the data of a plurality of generated element distribution images. The CPU 31 is capable of performing, based on the image data, the processing of sequentially displaying a plurality of element distribution images on the display unit 36 in the order corresponding to the elapsed time represented by the time information associated with the data of each element distribution image. By this processing, changes of the element distribution according to the passage of time are displayed on the display unit 36. Consequently, temporal changes of the element distribution image can be observed. For example, an element moving in the sample S can be observed. Moreover, the X-ray analyzer is capable of performing the processing of sequentially displaying a plurality of element distribution images on the display unit 36 at time intervals the same as the time intervals at which the element distribution images are generated, according to the elapsed time represented by the time information associated with the data of each element distribution image. By this processing, temporal changes of the element distribution image can be observed on the time scale the same as that of the changes caused in the sample S. Moreover, the X-ray analyzer is capable of performing the processing of changing the time intervals at which a plurality of element distribution images are displayed after making the same the ratio of the time intervals at which the element distribution images are generated and the ratio of the time intervals at which a plurality of element distribution images are displayed. By this processing, temporal changes of the element distribution image can be displayed on fast-forward and in slow motion.

Moreover, as mentioned previously, the X-ray analyzer is capable of moving the sample S concurrently with the scanning of the sample S. By sequentially displaying on the display unit 36 a plurality of element distribution images obtained from the moving sample S, temporal changes of a moving distribution of an element are displayed on the display unit 36. Consequently, the moving sample S can be observed by the X-ray analysis.

Moreover, the X-ray analyzer is capable of heating the sample S by using the heater 15. The CPU 31 outputs a control signal to the power supplier 23 in response to an instruction accepted by the operation unit 35 by a user operation, the power supplier 23 supplies power to the heater 15 according to the control signal, the heater 15 generates heat, so that the sample S is heated. Thus, the combination of heater 15 and power supplier 23 is one possible example of a change creating unit. The X-ray analyzer is capable of obtaining a plurality of element distribution images while performing the processing of heating the sample S concurrently with the scanning of the sample S. By sequentially displaying on the display unit 36 a plurality of element distribution images obtained from the heated sample S, temporal changes of the element distribution by heat are displayed on the display unit 36. Consequently, temporal changes of the element distribution image by heat can be observed. For example, a printed circuit board is used as the sample S and by heating the printing circuit board, a phenomenon can be observed in which a specific element contained in a wiring pattern on the printed circuit board diffuses to cause a break or a short circuit.

The X-ray analyzer may adopt a mode of having a function for creating a physical change other than a thermal change on the sample S. For example, the X-ray analyzer may adopt a mode of having the function of applying an external stress to the sample S such as an actuator. In this mode, a physical change such as a deformation according to the external stress occurs on the sample S, and temporal changes of the element distribution image can be observed. Specifically, a lead-free solder part on the board is used as the sample S and by applying an external stress to the lead-free solder part, a phenomenon can be observed in which whiskers occur on the lead-free solder part. Moreover, for example, the X-ray analyzer may adopt a mode of having an electrode and a power source for applying a voltage to the sample S. In this mode, a physical change according to the applied voltage occurs on the sample S, and temporal changes of the element distribution image can be observed.

Moreover, the X-ray analyzer may adopt a mode of having a function for creating a chemical change on the sample S. For example, the X-ray analyzer may adopt a mode of having a mixer that mixes a different liquid or drug into the sample S while controlling the mass or the speed. In this mode, a chemical change occurring on the sample S when a different liquid or drug is mixed in the sample S can be observed. Moreover, for example, the X-ray analyzer may adopt a mode of having a light emitter that emits light to the sample S. In this mode, changes of the physical properties of the sample S according to the light emission can be observed. Moreover, when the sample S is a catalyst, a catalytic reaction can be observed by using the X-ray analyzer.

Moreover, the X-ray analyzer is not limited to the mode of displaying the element distribution image on the display unit 36, but may adopt a mode of displaying the element distribution image on an external display device. For example, the X-ray analyzer may adopt a mode of being capable of transmitting image data to an external display device by using a non-illustrated interface. The external display device is capable of displaying the element distribution image based on the transmitted image data. Moreover, for example, the X-ray analyzer may adopt a mode of being capable of recording the image data on a recording medium by the drive unit 33. The external display device is capable of displaying the element distribution image based on the image data recorded on the recording medium.

The signal processor 21 may adopt a mode of executing part of the processing of the controller 3 described in the present embodiment, and the controller 3 may adopt a mode of executing part of the processing of the signal processor 21 described in the present embodiment. Moreover, the X-ray analyzer may adopt a mode in which the signal processor 21 and the controller 3 are integrated with each other. Moreover, as the information representative of the sequential order of generation of the element distribution images, the X-ray analyzer may store data representative of the order of generation of the element distribution images or may store the data representative of the time intervals at which the element distribution images are generated as well as the data representative of the order. Moreover, the X-ray analyzer according to the present embodiment may adopt a mode of being incorporated in an SEM (scanning electron microscope) or a TEM (transmission electron microscope). In this mode, the X-ray analyzer is provided with, for the SEM and for the TEM, a detector that detects an electron such as a reflection electron, a secondary electron or a transmission electron and a signal processor that processes the signal from the detector.

(Embodiment 2)

Figure 4:
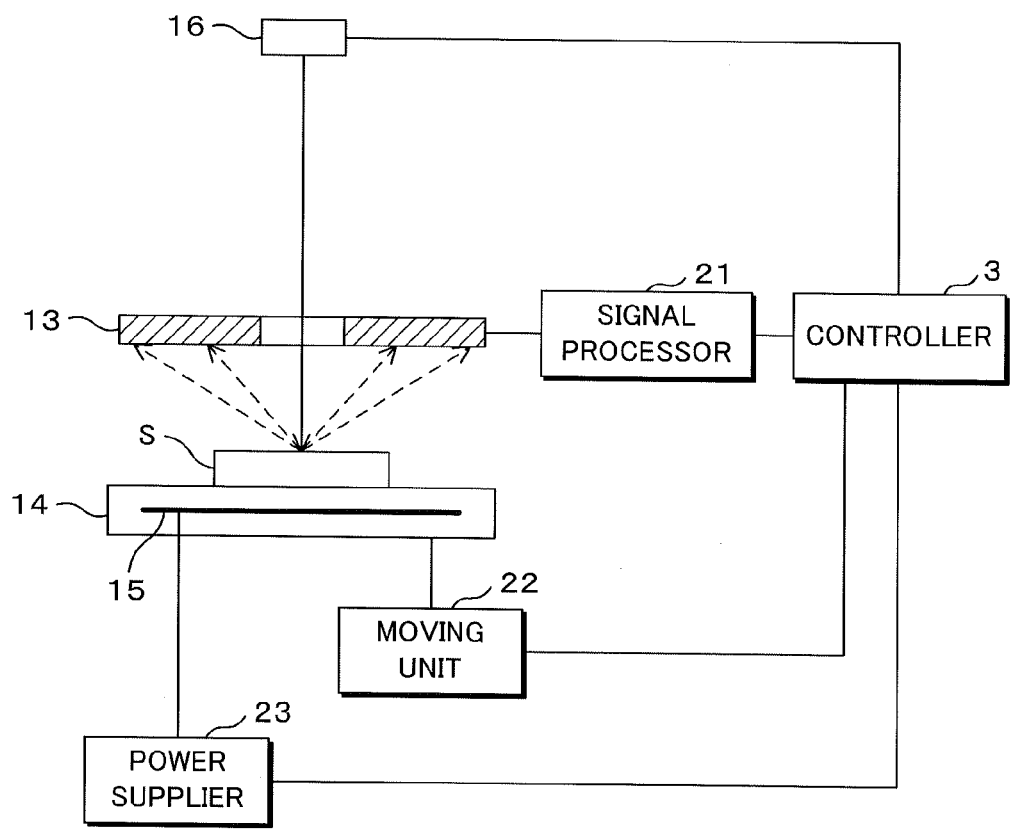
FIG. 4 is a block diagram showing the configuration of an X-ray analyzer according to Embodiment 2.

FIG. 4 is a block diagram showing the configuration of an X-ray analyzer according to Embodiment 2. The X-ray analyzer is not provided with the electron gun 11 and the electron lens system 12, and is provided with an X-ray source (beam source) 16. The X-ray source 16 is configured by using an X-ray tube. The X-ray source 16 applies an X-ray beam to the sample S on the stage 14. The X-ray detector 13 is disposed between the X-ray source 16 and the stage 14, and detects the X-ray fluorescence generated on the sample S by the application of the X-ray beam. The signal processor 21 obtains the spectrum of the X-ray fluorescence based on the signal outputted by the X-ray detector 13. Moreover, under a condition where the sample S is irradiated with the X-ray beam, the controller 3 controls the operation of the moving unit 22 to move the stage 14 in the horizontal direction, thereby executing the processing of scanning the sample S by the X-ray beam. The controller 3 and the moving unit 22 correspond to the scanning unit of the present invention. The signal processor 21 generates an element distribution image representative of the distribution of the elements on the sample S based on the spectrum of the X-ray fluorescence. The other components of the X-ray analyzer are similar to those of Embodiment 1.

As in Embodiment 1, the X-ray analyzer executes the processing at steps S1 to S5. In the present embodiment, the range where the element distribution image is to be obtained can also be positioned on the sample S based on the element distribution image itself. Likewise, the X-ray analyzer is capable of displaying temporal changes of the element distribution. Moreover, the X-ray analyzer is capable of performing the processing of moving the stage 14 in order to shift the scanning range on the sample S as well as moving the stage 14 for scanning. Consequently, in the present embodiment, the X-ray analyzer is also capable of displaying temporal changes of a moving distribution of an element. Further, in the present embodiment, the X-ray analyzer is also capable of heating the sample S by use of the heater 15 and displaying temporal changes of the element distribution by heating. Likewise, the X-ray analyzer may adopt a mode of having a function for creating a physical or a chemical change other than a thermal change on the sample S.

The X-ray analyzer may have a non-illustrated X-ray optical system for directing the X-ray beam to the sample S. Moreover, the X-ray analyzer may adopt a mode of having an X-ray source other than the X-ray source 16 using an X-ray tube, such as an X-ray source using an accelerator. While a mode of applying an electron beam to the sample S is shown in Embodiment 1 and a mode of applying an X-ray beam to the sample S is shown in Embodiment 2, the X-ray analyzer may adopt a mode of having a different beam source that emits a different beam for irradiating the sample S. For example, the X-ray analyzer may adopt a mode of having a beam source that emits a charged particle beam. Moreover, while a mode of having as the sample holder the stage 14 where the sample S is mounted is shown in Embodiment 1 and 2, the X-ray analyzer may adopt a mode of having a sample holder that holds the sample by a method other than mounting.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. An X-ray analyzer, comprising:
   a beam source;
   a sample holder;
   a scanning unit structured to scan repetitively a sample held by the sample holder, by a beam from the beam source;
   an X-ray detector that is disposed in a position between the beam source and the sample holder, comprising:
      a hole for passing the beam; and
      a plurality of X-ray sensors disposed around the hole,
      wherein the X-ray detector is structured to detect an X-ray generated on the sample scanned by the scanning unit;
   a generation unit structured to generate an element distribution image representative of a distribution of an element contained in the sample, based on a result of the detection by the X-ray detector, every time the scanning unit scans the sample; and
   a storage unit structured to store a plurality of element distribution images generated by the generation unit, in associated with information representative of a sequential order of generation of the element distribution images.

2. The X-ray analyzer according to claim 1, further comprising:
   a display unit; and
   a clock unit structured to measure a time elapsed from a specific time point,
   wherein the storage unit is structured to store information representative of the measured elapsed time as the information representative of the sequential order, and
   the display unit is structured to sequentially display the element distribution images stored in the storage unit according to the measured elapsed time.

3. The X-ray analyzer according to claim 2,
   wherein the display unit is structured to display the element distribution image generated by the generation unit and update the displayed element distribution image every time the generation unit generates the element distribution image.

4. The X-ray analyzer according to claim 3, further comprising:
   an accept unit structured to accept an instruction for moving the sample;
   a moving unit structured to move the sample holder; and
   a shifting unit structured to shift a position to be scanned by the scanning unit on the sample, by causing the moving unit to move the sample holder according the instruction accepted by the accept unit so as to move the sample.

5. The X-ray analyzer according to claim 2, further comprising
   a moving unit structured to move the sample holder concurrently with the operations of the scanning unit and the generation unit.

6. The X-ray analyzer according to claim 1, further comprising
   a moving unit structured to move the sample holder concurrently with the operations of the scanning unit and the generation unit.

7. The X-ray analyzer according to claim 1, further comprising
a change creating unit structured to create a physical or a chemical change on the sample held by the sample holder concurrently with the operations of the scanning unit and the generation unit.

* * * * *